United States Patent [19]
Scott

[11] Patent Number: 6,106,495
[45] Date of Patent: Aug. 22, 2000

[54] METHODS AND APPARATUS FOR DELIVERING ANTIBIOTIC POWDERS INTO THE FEMORAL CANAL FOR THE REDUCTION OF ORTHOPAEDIC SEPSIS DURING TOTAL HIP ARTHROPLASTY

[75] Inventor: Christopher P. Scott, Hackensack, N.J.

[73] Assignee: Howmedica Inc., New York, N.Y.

[21] Appl. No.: 09/081,963

[22] Filed: May 20, 1998

[51] Int. Cl.[7] .................................................. A61M 11/00
[52] U.S. Cl. ................. 604/93; 604/58; 604/506
[58] Field of Search .................... 606/60, 62; 623/16, 623/22; 604/175, 93, 82, 84, 142, 151, 173, 181, 163, 501, 502, 506, 507, 890.1, 892.1, 58

[56] References Cited

U.S. PATENT DOCUMENTS

| | | | |
|---|---|---|---|
| 5,112,303 | 5/1992 | Pudenz et al. | 604/502 |
| 5,542,412 | 8/1996 | Century | 604/58 X |
| 5,616,121 | 4/1997 | McKay | 604/93 X |
| 5,681,289 | 10/1997 | Wilcox et al. | 604/175 |
| 5,787,900 | 8/1998 | Butler et al. | 604/93 X |
| 5,800,408 | 9/1998 | Strauss et al. | 604/93 X |
| 5,899,880 | 5/1999 | Bellhouse et al. | 604/70 |

*Primary Examiner*—Wynn Wood Coggins
*Assistant Examiner*—A. T. Nguyen
*Attorney, Agent, or Firm*—Lerner, David, Littenberg, Krumholz & Mentlik, LLP

[57] ABSTRACT

Methods and apparatus of the present invention include encapsulating the antibiotic in fine particles of bioabsorbable polymer which will yield a constant dissolution of the antibiotic over a predefined dosing period (such as a 7–10 day period), with residual antibiotic being thereafter delivered only until the bioabsorable polymer is resorbed; and delivering the fine particle powder to the surgical site as an aerosol spray. It is preferable that the antibiotic and the polymer be thermostable so that the exothermic reaction of bone cement does not degrade the polymer or the antibiotic. A suitable antibiotic for this purpose is an aminoglycoside. One apparatus according to the invention include a porous delivery tube which is dimensioned to fit comfortable in a bone canal and which is coupled to a aerosol canister containing the antibiotic powder of the invention. Another apparatus according to the invention includes a porous delivery tube which is preloaded with measured amounts of antibiotic powder and which is adapted to be coupled to a source of compressed air.

24 Claims, 2 Drawing Sheets

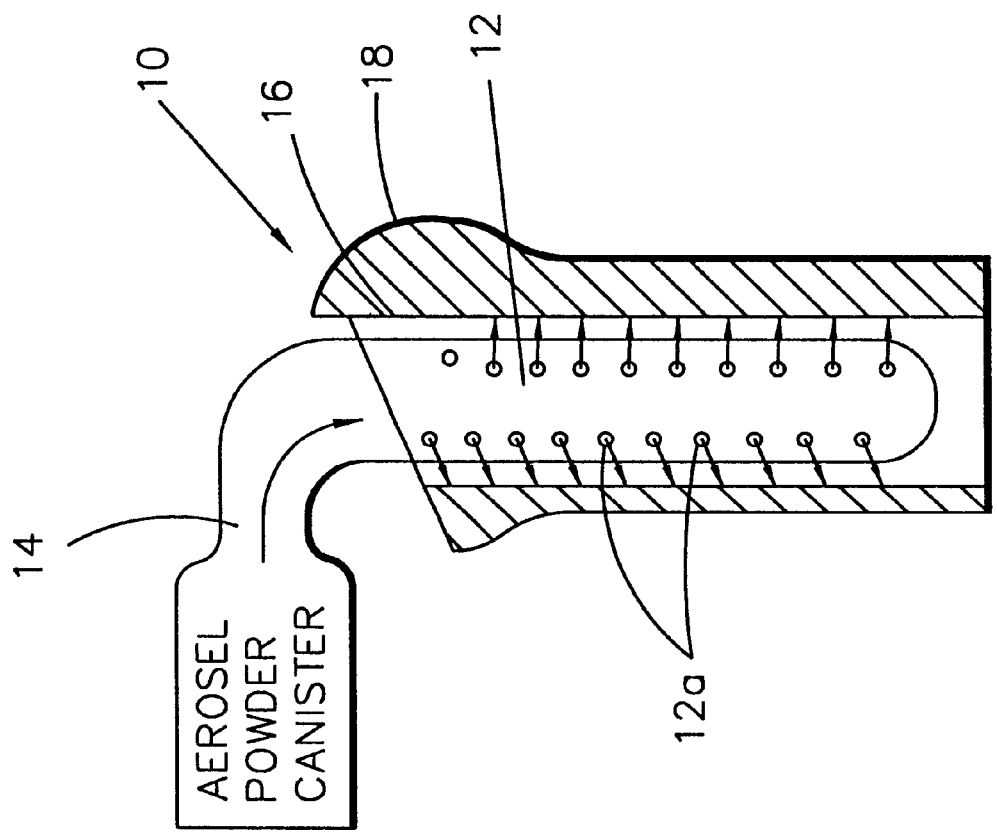

METHODS AND APPARATUS FOR DELIVERING ANTIBIOTIC POWDERS INTO THE FEMORAL CANAL FOR THE REDUCTION OF ORTHOPAEDIC SEPSIS DURING TOTAL HIP ARTHROPLASTY

BACKGROUND OF THE INVENTION

1. Field of the Invention

The invention relates to methods and apparatus for dispensing medication at a surgical site. More particularly, the invention relates to methods and apparatus for dispensing antibiotics at an orthopaedic surgical site.

2. Brief Description of the Related Art

In open surgical procedures, it is common to apply an antibiotic, analgesic, growth stimulator, or other chemical agent at the surgical site prior to closing the incision in order to control infection, decrease pain, promote growth, etc.

One of the most devastating complications of total joint arthroplasty is deep sepsis. Treatment of an infected joint replacement is difficult due to its location, and localized devascularization resulting from this procedure.

Current approaches to therapy for deep infections include systemic or parenteral antibiotic regimes, and the use of antibiotic impregnated acrylic bone cement. Due to the localized devascularization it is difficult to achieve therapeutic levels in the bone surrounding the implant without exceeding toxic serum concentrations when utilizing systemic or parenteral treatments. The use of antibiotic containing bone cement results in high local concentrations, while avoiding toxic serum levels, but the antibiotic has been shown to elute in trace quantities for extended periods of time (greater than one year). Residual trace amounts of antibiotics have raised concerns of resistant strain formation. An additional concern regarding adding antibiotics to bone cement is the possible degradation of mechanical properties of the bone cement whose primary function is as a fixation material.

According to the state of the art, it is preferable to apply therapeutic concentrations at the surgical site for a period of 7 to 10 days, with no residual antibiotics lingering for extended periods of time. It is also desirable to achieve these high local concentrations without elevating serum concentrations, thus reducing the threat of systemic toxicity. A means of antibiotic treatment that can be utilized for joint replacement procedures that either involve the use of bone cement or not is desirable as well.

U.S. Pat. No. 5,681,289 to Wilcox et al. discloses a dispensing bladder for passing a low volume flow of a liquid chemical agent at an orthopaedic surgical site. The bladder is installed adjacent to or as part of an orthopaedic implant. It is coupled to a tube which receives a supply of liquid chemical such as an antibiotic via an injection port or an implanted or external reservoir and pump.

The bladder may be biodegradable so as to avoid the need for extensive surgery to remove it. However, the tube, injection site, pump, and reservoir must be surgically removed. Moreover, it is believed that the delivery of a liquid antibiotic in the femoral canal may degrade the mechanical properties of bone cement on an implant stem.

SUMMARY OF THE INVENTION

It is therefore an object of the invention to provide a method and apparatus for delivering an antibiotic to an orthopaedic surgical site.

It is also an object of the invention to provide a method and apparatus for delivering an antibiotic to an orthopaedic surgical site which does not require an additional implant which must subsequently be surgically removed.

It is another object of the invention to provide a method and apparatus for delivering an antibiotic to an orthopaedic surgical site which will deliver a therapeutic dose of antibiotic over a predefined dosing period, for example 7–10 days.

It is still another object of the invention to provide a method and apparatus for delivering an antibiotic to an orthopaedic surgical site which will not interfere with the mechanical properties of bone cement.

Another object of the invention is to provide a method and apparatus for delivering an antibiotic to an orthopaedic surgical site which does not leave long term residual antibiotics at the site after the dosing period.

Another object of the invention is to provide methods and apparatus for delivering an antibiotic to an orthopaedic surgical site which do not significantly elevate serum levels.

In accord with these objects which will be discussed in detail below, the methods and apparatus of the present invention include encapsulating the antibiotic in fine particles of bioabsorbable polymer which will yield a constant dissolution of the antibiotic over a predefined dosing period (such as a 7–10 day period), with residual antibiotic being thereafter delivered only until the bioabsorbable polymer is resorbed; and delivering the fine particle powder to the surgical site as an aerosol spray.

It is preferable that the antibiotic and the polymer be thermostable so that the exothermic reaction of bone cement does not degrade the polymer or the antibiotic.

A suitable antibiotic for this purpose is an aminoglycoside and a suitable polymer is poly lactide-co-glycolide (PLGA).

In situations where themostability is not an issue, for example where bone cement is not used, then virtually any antibiotic may be delivered via the techniques taught herein, such as (without limitation), penicillin, etc. Furthermore, those skilled in the art will readily appreciate that other bioabsorable polymers can be readily substituted for PLGA, for example (without limitation), PLA, etc.

One apparatus according to the invention includes a porous delivery tube which is dimensioned to fit comfortably in a bone canal and which is coupled to a aerosol canister containing the antibiotic powder of the invention.

Another apparatus according to the invention includes a porous delivery tube which is pre-loaded with measured amounts of antibiotic powder and which is adapted to be coupled to a source of compressed air.

Additional objects and advantages of the invention will become apparent to those skilled in the art upon reference to the detailed description taken in conjunction with the provided figures.

BRIEF DESCRIPTION OF THE DRAWING

FIG. 1 is a schematic sectional view of a first embodiment of an antibiotic delivery apparatus according to the invention;

DETAILED DESCRIPTION

Figure 3:
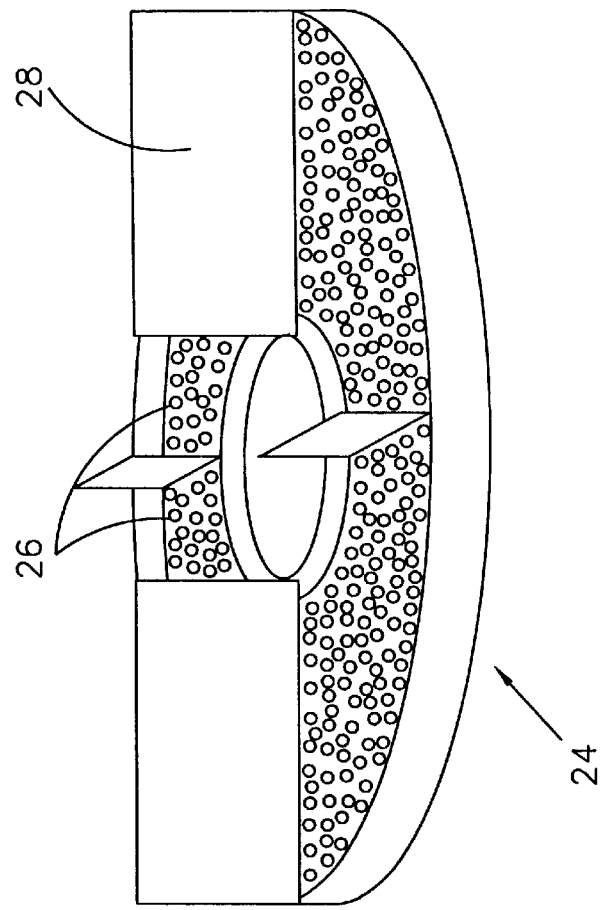
FIG. 3 is an enlarged perspective view of a component of the antibiotic delivery apparatus of FIG. 2.
Figure 2:
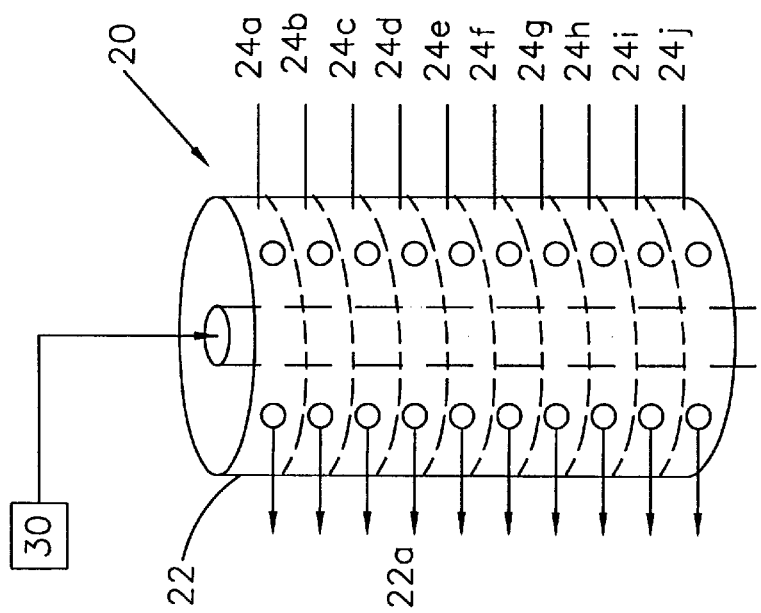
FIG. 2 is a schematic perspective view of a second embodiment of an antibiotic delivery apparatus according to the invention.

According to the invention, a powdered antibiotic is manufactured by encapsulating antibiotic in fine particles of bioabsorbable polymer.

Suitable processes for encapsulating an antibiotic in a resorbable powder are disclosed in the following nine journal articles, the complete disclosures of which are hereby incorporated herein by reference:

(a) Van Hamont, J. E. et al., "Evaluation of Solvent Extraction and Solvent Evaporation Procedures for Production of Tobramycin-Releasing Microspheres," Proceed. Intern. Symp. Control. Rel. Bioact. Mater., 23 (1996), Controlled Release Society, Inc.

(b) Martinez, B. et al., "Tetracine Release from Biodegradable Microspheres," Proceed. Intern. Symp. Control. Rel. Bioact. Mater., 27 (1997), Controlled Release Society, Inc.

(c) Kim, J. H. et al., "The Modified Solvent Extraction Method on the Preparation of Poly(L-Lactic Acid) Microspheres," Proceed. Intern. Symp. Control. Rel. Bioact. Mater., 24 (1997), Controlled Release Society, Inc.

(d) Bittner, B. et al., "Preparation of Protein-Loaded Poly (Lactide-Co-Glycolide) Microspheres Using an Ultrasonic Atomizer," Proceed. Intern. Symp. Control. Rel. Bioact. Mater., 24 (1997), Controlled Release Society, Inc.

(e) Takada, S., "Novel Microencapsulation Technique for Controlled Release of a Water-Soluble Non-Basic Drug," Proceed. Intern. Symp. Control. Rel. Bioact. Mater., 23 (1996), Controlled Release Society, Inc.

(f) Jeyanthi, R. et al., "Novel Burst Free Programmable Biodegradable Microspheres for Controlled Release of Polypeptides," Proceed. Intern. Symp. Control. Rel. Bioact. Mater., 23 (1996), Controlled Release Society, Inc.

(g) Witschi, C., "Influence of the Preparation Method and Polymer Composition on Peptide Adsorption and Peptide Release from Biodegradable Microparticles During In Vitro Release," Proceed. Intern. Symp. Control. Rel. Bioact. Mater., 24 (1997), Controlled Release Society, Inc.

(h) Van Hamont, J. E. et al., "Effect of PLGA End Groups on Encapsulation and Release of Tobramycin from Microspheres Produced by Organic Processes," Proceed. Intern. Symp. Control. Rel. Bioact. Mater., 24 (1997), Controlled Release Society, Inc.

(i) Grandfils, C. et al., "Control of the Biodegradation Rate of Poly(DL-Lactide) Microparticles Intended as Chemoembolization Materials," Journal of Controlled Release 38 (1966).

The prepared antibiotic powder, when placed at a surgical site will yield a constant dissolution of the antibiotic over a period of 7–10 days.

Turning now to FIG. 1, an apparatus 10 according to the invention for delivering the powdered antibiotic to an orthopaedic surgical site includes a porous tube 12 which is coupled to an aerosol container 14 which contains a measured amount of the powdered antibiotic for a single procedure.

According to a presently preferred illustrative embodiment, the tube 12 is dimensioned to fit comfortable in the intermedullary canal 16 of the femur 18. The tube 12 is made of a biocompatible material such as plastic or stainless steel and is made porous by perforations 12*a* which are evenly spaced about the tube 12.

The apparatus is used during an orthopaedic procedure after the femoral canal 16 is prepared, before the prosthetic implant is installed.

The apparatus 10 is operated by inserting the tube 12 into the IM canal 16 of the femur 18 and opening a valve (not shown) on the aerosol container 14.

The aerosol forces the antibiotic powder into the tube 12 and out through the perforations 12*a* into the wall of the IM canal 16.

According to a presently preferred embodiment, the aerosol container 14 contains enough powder and propellant for one application and is disposable after one use. After the aerosol is depleted, the apparatus 10 is removed from the femur and the prosthetic implant is installed in a conventional manner.

The antibiotic powder which was delivered to the IM canal will not interfere with bone cement, will dissolve a therapeutic level of antibiotic into the femur continuously over 7–10 days and will not leave long time residual antibiotics in the femur.

Turning now to FIGS. 2 and 3, another apparatus 20 according to the invention includes a porous delivery tube 22 which is pre-loaded with measured amounts of antibiotic powder 26 and which is adapted to be coupled to a source of compressed air 30.

The tube 22 may be made of biocompatible plastic or stainless steel which may be made porous by perforations 22*a* which are evenly spaced along the length of the tube.

According to this illustrative embodiment of the invention, a plurality of annular shelves 24 (e.g., 24*a*–24*j*) are arranged inside the tube 22 axially spaced apart from each other as shown in FIG. 2. Each shelf 24 carries a measured amount of antibiotic powder 26 as shown in FIG. 3.

According to a preferred embodiment, each shelf 24 has a plurality of orthogonal fins 28 which aid in stacking the shelves inside the tube 22 and directing the flow of powder 26 out of the perforations 22*a*.

The apparatus 20 is operated by inserting the tube 22 into the IM canal of the femur, attaching a source 30 of compressed air to the tube and forcing compressed air into the tube. The compressed air forces the antibiotic powder 26 off of the shelves 24 and out through the perforations 22*a* into the wall of the IM canal.

According to a presently preferred embodiment, the shelves 24 contain enough powder 26 for one application and the apparatus 20 is disposable after one use. After a measured period of dispensing, the apparatus 20 is removed from the femur and the prosthetic implant is installed in a conventional manner.

The antibiotic powder which was delivered to the IM canal will not interfere with bone cement, will dissolve a therapeutic level of antibiotic into the femur continuously over 7–10 days and will not leave long time residual antibiotics in the femur.

There have been described and illustrated herein several embodiments of a method and apparatus for delivering antibiotic powder to the IM canal of the femur.

While particular embodiments of the invention have been described, it is not intended that the invention be limited thereto, as it is intended that the invention be as broad in scope as the art will allow and that the specification be read likewise. Thus, while particular powders have been disclosed, it will be appreciated that other powders could be utilized. Also, while the invention has been disclosed for use in the IM canal of the femur, it will be understood that the invention may have utility in dispensing medication in other bone canals.

It will therefore be appreciated by those skilled in the art that yet other modifications could be made to the provided invention without deviating from its spirit and scope as so claimed.

What is claimed is:

1. An apparatus for dispensing medication into a bone canal, said apparatus comprising:

(a) a porous tube dimensioned to fit into the bone canal;

(b) a powdered medication deliverable through said porous tube; and (c) fluid pressure means coupled to said tube means for forcing said powdered medication through said porous tube.

2. An apparatus according to claim 1 wherein said fluid pressure means comprises an aerosol container and said powdered medication is contained within said aerosol container.

3. An apparatus according to claim 1 wherein said powdered medication is contained within said porous tube and said fluid pressure means is detachable from said porous tube.

4. An apparatus according to claim 3 wherein said porous tube includes a plurality of annular shelves and said powdered medication is contained on said shelves.

5. An apparatus according to claim 4 wherein each of said annular shelves has a plurality of orthogonal vanes.

6. An apparatus according to claim 1 wherein said powdered medication is an antibiotic encapsulated in a bioabsorbable polymer in such a way as to yield constant dissolution over a predefined therapeutic dosing period with residual antibiotic being delivered thereafter only until said bioabsorbable polymer is resorbed.

7. Apparatus as set forth in claim 6 wherein said predefined therapeutic dosing period is 7–10 days.

8. An apparatus according to claim 1 wherein said powdered medication is thermostable when exposed to an exothermic reaction of orthopaedic bone cement.

9. An apparatus according to claim 7 wherein said antibiotic is an aminoglycoside.

10. An apparatus according to claim 7 wherein said bioabsorbable polymer is poly lactide-co-glycolide (PLGA).

11. An apparatus for dispensing medication into a bone canal, said apparatus comprising:

(a) a porous tube dimensioned to fit into the bone canal;

(b) an aerosol container coupled to said porous tube; and (c) a powdered medication contained in said aerosol container and deliverable through said porous tube.

12. An apparatus according to claim 11 wherein said porous tube is one of a perforate plastic tube and a perforate stainless steel tube.

13. An apparatus according to claim 11 wherein said powdered medication is an antibiotic encapsulated in a bioabsorbable polymer in such a way as to yield constant dissolution over a predefined therapeutic dosing period with residual antibiotic being delivered thereafter only until said bioabsorbable polymer is resorbed.

14. Apparatus as set forth in claim 13 wherein said predefined therapeutic dosing period is 7–10 days.

15. An apparatus according to claim 11 wherein said powdered medication is thermostable when exposed to an exothermic reaction of orthopaedic bone cement.

16. An apparatus according to claim 13 wherein said antibiotic is an aminoglycoside.

17. An apparatus according to claim 13 wherein said bioabsorbable polymer is poly lactide-co-glycolide (PLGA).

18. A method for dispensing a medication into a bone canal, said method comprising the steps of:

(a) inserting a porous tube into the bone canal;

(b) attaching a source of fluid pressure to the tube;

(c) prior to attaching, arranging a supply of powdered medication between the tube and the source of fluid pressure; and (d) releasing fluid pressure into the tube such that the powdered medication is forced out of the tube into the bone canal.

19. A method according to claim 18 wherein said step of attaching includes attaching an aerosol container to the tube.

20. A method according to claim 19 wherein said step of arranging include placing the powdered medication in the aerosol container.

21. A method according to claim 18 wherein said step of attaching includes attaching the tube to a source of compressed air.

22. A method according to claim 21 wherein said step of arranging includes storing the powdered medication inside the tube.

23. A method according to claim 22 wherein said step of storing includes providing a plurality of shelves inside the tube and placing measured amounts of the powdered medication on each shelf.

24. An apparatus for dispensing medication into a bone canal, said apparatus comprising:

(a) a porous tube dimensioned to fit into the bone canal;

(b) a powdered medication deliverable through said porous tube, said powdered medication being disposed in a plurality of locations within said tube; and (c) fluid coupling means for coupling said tube to a source of fluid pressure for forcing said powdered medication through said porous tube.

\* \* \* \* \*

UNITED STATES PATENT AND TRADEMARK OFFICE
CERTIFICATE OF CORRECTION

PATENT NO. : 6,106,495

DATED : August 22, 2000

INVENTOR(S) : Scott

Page 1 of 3

It is certified that error appears in the above-identified patent and that said Letters Patent is hereby corrected as shown below:

On the face of the patent:

In the Assignee Section:
"Howmedica Inc., New York, N.Y." should read -- Stryker Technologies Corporation of Kalamazoo, Michigan --

Column 5, line 3, cancel the word "means" (second occurrence).
Column 5, line 5, cancel the ".";
Column 5, line 5, after "tube" insert -- ; wherein --.
Column 5, before line 6, insert -- (d) said porous tube includes a plurality of annular shelves and said powdered medication is contained on said shelves. --.
Column 5, cancel claim 4.
Column 5, line 17, "5" should read -- 4 --.
Column 5, line 17, "4" should read -- 3 --.
Column 5, line 19, "6" should read -- 5 --.
Column 5, line 25, "7" should read -- 6 --.
Column 5, line 25, "6" should read -- 5 --.
Column 5, line 27, "8" should read -- 7 --.
Column 5, line 30, "9" should read -- 8 --.
Column 5, line 30, "7" should read -- 6 --.
Column 5, line 32, "10" should read -- 9 --.
Column 5, line 32, "7" should read -- 6 --.
Column 5, line 34, "11" should read -- 10 --.
Column 5, line 39, cancel the "."
Column 5, line 39, after "tube" insert -- ; wherein --.
Column 5, before line 40, insert -- (d) said porous tube includes a plurality of annular shelves and said powdered medication is contained on said shelves. --

UNITED STATES PATENT AND TRADEMARK OFFICE
CERTIFICATE OF CORRECTION

PATENT NO. : 6,106,495
DATED : August 22, 2000
INVENTOR(S) : Scott

It is certified that error appears in the above-identified patent and that said Letters Patent is hereby corrected as shown below:

Column 5, line 40, "12" should read -- 11 --.
Column 5, line 40, "11" should read -- 10 --.
Column 5, line 43, "13" should read -- 12 --.
Column 5, line 43, "11" should read -- 10 --.
Column 6, line 3, "14" should read -- 13 --.
Column 6, line 3, "13" should read -- 12 --.
Column 6, line 5, "15" should read -- 14 --.
Column 6, line 5, "11" should read -- 10 --.
Column 6, line 8, "16" should read -- 15 --.
Column 6, line 8, "13" should read -- 12 --.
Column 6, line 10, "17" should read -- 16 --.
Column 6, line 10, "13" should read -- 12 --.
Column 6, line 12, "18" should read -- 17 --.
Column 6, line 18, after "pressure;", insert -- wherein said porous tube includes a plurality of annular shelves and said powdered medication is contained on said shelves; --
Column 6, line 21, "19" should read -- 18 --.
Column 6, line 21, "18" should read -- 17 --.
Column 6, line 23, "20" should read -- 19 --.
Column 6, line 23, "19" should read -- 18 --.

UNITED STATES PATENT AND TRADEMARK OFFICE
CERTIFICATE OF CORRECTION

PATENT NO. : 6,106,495
DATED : August 22, 2000
INVENTOR(S) : Scott

It is certified that error appears in the above-identified patent and that said Letters Patent is hereby corrected as shown below:

Column 6, line 26, "21" should read -- 20 --.
Column 6, line 26, "18" should read -- 17 --.
Column 6, line 29, "22" should read -- 21 --.
Column 6, line 29, "21" should read -- 20 --.
Column 6, line 32, "23" should read -- 22 --.
Column 6, line 32, "22" should read -- 21 --.
Column 6, line 36, "24" should read -- 23 --.
Column 6, line 45, cancel the ".";
Column 6, line 45, after "tube" insert -- ; wherein --
Column 6, after line 45, insert -- (d) said porous tube includes a plurality of annular shelves and said powdered medication is contained on said shelves. --

Signed and Sealed this

Twenty-second Day of May, 2001

Attest:

NICHOLAS P. GODICI

Attesting Officer

Acting Director of the United States Patent and Trademark Office